United States Patent [19]

Wittmann, nee Liebold et al.

[11] 3,959,307

[45] May 25, 1976

[54] METHOD TO DETERMINE AUTOMATICALLY THE SEQUENCE OF AMINO ACIDS

[76] Inventors: Brigitte Wittmann, née Liebold, Meisenstrasse 17; Horst Graffunder, Lutzelsteiner Weg 52, both of 1000-Berlin 33, Germany

[22] Filed: Feb. 15, 1974

[21] Appl. No.: 442,852

[52] U.S. Cl. .......................... 260/309.5; 23/230 M; 23/252 R
[51] Int. Cl.² ....................................... C07D 49/32
[58] Field of Search ............................... 260/309.5

[56] References Cited
OTHER PUBLICATIONS

Edman, P., Acta Chem. Scand. 4, (1950), pp. 277–282.
Ilse et al., Austral. Journ. Chem. 16, (1963), pp. 411–416.
Edman, P., Acta Chem. Scand. 10 (1956), pp. 761–768.
Wittman-Liebold, Hoppe-Seylers Zeitschrift fuer Physiologische Chemie, Bd. 354, pp. 1415–1431, 10–11/1973.
Edman et al., European Journal of Biochemistry, vol. 1, pp. 80–91 (1967).
Edman, Royal Australian Chemical Institute, Proceedings, 1957.

Primary Examiner—Ethel G. Love
Attorney, Agent, or Firm—Christen & Sabol

[57] ABSTRACT

Method and apparatus for automatically converting of thiazolinone amino acids into phenyl thiohydantoin amino acids as a stage in amino acid sequence analysis of proteins and peptides. According to the invention a solution of thiazolinone amino acids is, under continuous exclusion of oxygen, introduced into a reaction vessel and evaporated to dryness. Then there is added an aqueous trifluoro acetic acid solution or dilute hydrochloric acid, containing a mercaptan, and again evaporated, followed by dissolving of the residue in a mixture of dichloroethane and methanol.

7 Claims, 1 Drawing Figure

U.S. Patent May 25, 1976 3,959,307
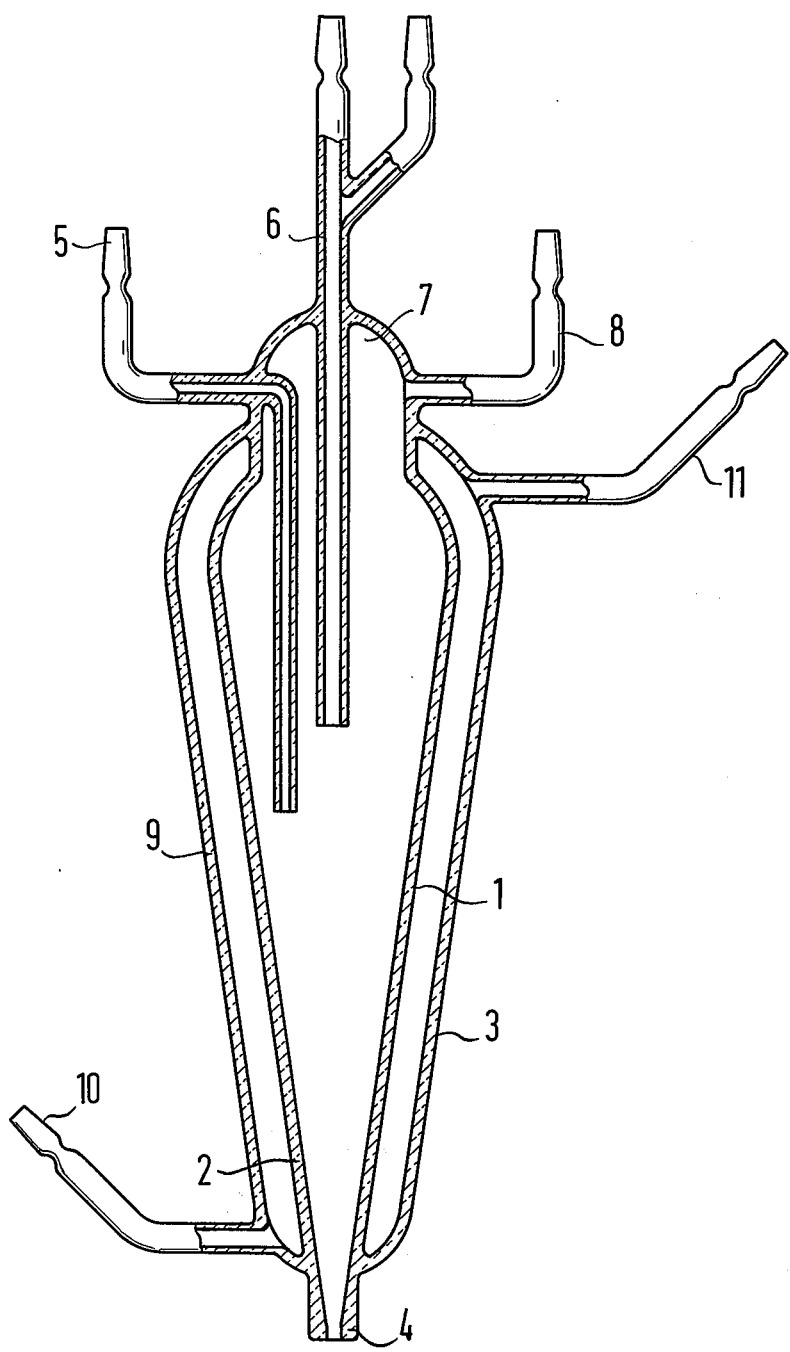

METHOD TO DETERMINE AUTOMATICALLY THE SEQUENCE OF AMINO ACIDS

The present invention relates to a method of automatically converting a Thiazolinone amino acid into a phenylthiohydantoin amino acid as a stage in the amino acid sequence analysis of proteins or peptides according to the method of Edman and Begg, and relates to an apparatus to perform the method.

The determination of the the amino acid sequence of peptides and proteins is of increasing practical and scientific importance. As this sequence analysis is very laborious, there have already been efforts to reduce the labour by developing automatic methods.

These so-called sequenators are breaking down peptides or proteins step by step from their N-terminal end according to the method of Edman and Begg. According to this method the free α-amino group to the N-terminal end is transferred into Phenylthiocarbamyl derivative at pH 10 by Phenylisothiocyanate. The derivative is detached and cyclizised to form a Thiazolinone derivative, which is converted by acid treatment into phenylisothiohydantoin derivative. The α-amino group of the amino acid following the first one in the chain is thereby disclosed and may be detached and identified in the same manner.

The sequenators, for several reasons are far superior to the manual stepwise degradation:

1. The degradation must be performed in the absence of oxygen.
2. A manual stepwise degradation requires about one day's work for each amino acid, while the automatic process requires some 2 hours.
3. As the course of the chemical reaction is endlessly repeated, an automatic apparatus makes possible a significantly more regular performance of the reaction: the degradation is successful to 97 to 98%.
4. Using a manually accomplished Edman-Begg degradation, it is only possible to determine about 5 to 10 amino acids, while when automated, 20 to 60 N-terminal amino acids can be determined as to their sequence.
5. When ascertaining the sequence of peptides about 20 amino acids can be determined, which however requires considerable amounts of substance. By means of the sequenators up to 30 amino acids may be degraded and quantitatively conceived; while considerably smaller amounts of substance can be used as compared to manual degradation.

It is an important fact that the degradation of proteins and peptides according to Edman and Begg comprises three stages, all of which must be carried out in the absence of oxygen, the stages being:

1. Addition of the reagent
2. Cyclization and
3. Conversion (Thiazolinone into Phenylthiohydantoin).

All sequenators available until now (Beckman Sequenator; Laursen Peptide-Sequenator) make possible an automatic performance of only the two first stages, i.e., addition of the reagent and cyclization. The amino acid, eliminated at each degradation step, is then transferred as unstable Thiazolinone, susceptible to oxygen and light, into a fraction collector, where it is stored until further manual conversion into a stable derivative, phenylthiohydantoin amino acid (PTH-AA), is carried out. The product is not achieved until this conversion, and the product is then finally identified, e.g. by thin layer chromatography, gas chromatography or mass spectrometry.

In spite of the technical improvements already achieved by automation of the subject method the disadvantage remains that the conversion has to be carried out manually. This process step is rather laborious. Due to the extraction of the PTH-AA, necessary after the conversion, two centrifugations have to be carried out, which is experimentally inconvenient when performed in the absence of oxygen. It is also impossible when using manual conversion to obtain identical experimental conditions for all degradation steps. The different thiazolinones are also decomposed at different rates. This will cause significant yield reduction and unwanted by-products, which will make the identification more difficult. The Thiazolinone obtained from the sequenator after the degradation step cannot immediately be rearranged manually into a stable PTH-AA derivative but only 1 to 2 times a day with 5 to 10 degradation steps, respectively, as the conversion otherwise will be two work-consuming. Especially the most sensitive Thiazolinones are in that way almost completely destroyed already during the storage time, e.g., the thiazolinones of serine, threonine, histidine, arginine and, cysteine.

In order to make this more understandable, described below is the manual conversion embodying the automatic apparatuses used heretobefore.

a. Degradation of Proteins

The apparatus provides the amino acids which are degraded from the protein an unstable Thiazolinones in a 1-Chlorobutane solution, which is stored in a fraction collector and partly evaporated, as the fraction collector is evacuated. At a temperature of 6° to 10°C the Thiazolinone is stored in this solution until further manual processing (emulsion) into the more stable PTH-amino acids the next morning. For manual conversion the sample vials of the fraction collector are evacuated to dryness (about 30 minutes) in nitrogen atmosphere, and incubated with 0.2 ml 1-N N hydrochloric acid under a nitrogen atmosphere for 10 minutes at 80°C. After cooling the PTH-amino acids formed must be recovered from the aqueous solution by extraction twice with ethyl acetic ester (2 × 0.7 ml) and correspondingly centrifugal twice (for about 1 hour). The combined extracts of ethyl acetic ester are evaporated under a nitrogen atmosphere to dryness (requires about 20 to 30 minutes) and are received in a small volume (50 μl) of ethyl acetic ester for further identification by gas chromatography and thin layer chromatography. As the apparatus is used for 12 degradation steps a day it will be appreciated that manual operation is time-consuming and cannot be performed without the exclusion of oxygen, especially during the centrifugation step. Furthermore, the derivatives of the amino acids argenine, cysteic acid, and histidine will remain in the aqueous phase and to be separately recovered. In the aqueous hydrochloric acid they are already mainly destroyed by the evaporation and the amount of substance is already, after 15 to 20 degradation steps, insufficient for unambiguous identification.

b. Degradation of Peptides

The automatic apparatus provides the Thiazolinone in Trifluoro acetic acid in methanol. This solution is stored in a fraction collector until further processing.

The conversion is carried out after evaporation of the solution in 20% aqueous Trifluoro acetic acid, having dithioerythrite added to it to protect the unstable Thiazolinone, for 10 minutes at 80°C. After the conversion, this solution is evaporated under a nitrogen atomosphere and is placed in methanol for further purification and identification of the PTH- amino acids.

Accordingly, it is an object of the present invention to provide a method for automatic performance of the conversion in order to avoid the above mentioned disadvantages of the manual conversion. The method of this invention is easily incorporated into the process of the existing automatic apparatuses and will also be suitable for possible new automatic machines. A further object of the present invention is to provide an apparatus, suitable to perform the method, which can be easily incorporated into existing automatic apparatuses so as to make possible a wholly automated sequence analysis.

The object of the present invention is accomplished by a method for automatically transforming thiazolinone amino acids into phenylthiohydantion amino acids in the field of amino acid sequence analysis of proteins or peptides by heating the thiazilinone amino acids for a short period of time in acidic solution with the exclusion of oxygen and transferring the residue into a solution proper for identification or further purification in an organic solvent. The method is characterized in that under continuous exclusion of oxygen, a solution of thiazolinone amino acid in the solvent, prior to its conversion, is introduced into a reaction vessel where it is evaporated to dryness at a temperature between 50 to 80°C and then there is added an aqueous trifluoro acetic acid solution having a mercaptan added to it, or dilute having a mercaptan added to it, in HCl such amount which at the prevailing constant temperature and flow through of inert gas will be completely evaporated within 30 to 40 minutes. The residue is dissolved by spraying over it a mixture of 6 to 8 parts of volume of 1,2 l dichloroethane 4 to 2 parts of volume of methanol and the solution thus obtained is withdrawn from the reaction vessel for further processing.

As the inert gas, nitrogen is preferably utilized, since in the existing automatic apparatuses the requirements for nitrogen supply are already fullfilled. However, other inert gases (e.g., helium or argon) may be used.

As the trifluoro acetic acid solution and containing 10 to 150 mg/l of dithioerythrite a 20% solution in water, is preferred, and as the diluted hydrochloric acid, a 1-N solution having a concentration of 10 to 150 mg/l of dithioerythrite as the SH-containing (mercapto containing) substance can be used. Other protective substances containing SH-groups, being at hand within biochemistry, may be used in a similar way (e.g. $\beta$-mercaptoethanol, ethane dithiol, butane dithiol and butane thiol can also be used).

The interval between 53° and 57°C is the most suitable temperature as the evaporation rate of the solvent and the rearrangement rate are approximately the same in this interval. The FIGURE is a cross-sectional view of the reactor cell (apparatus) according to this invention for performance of the method of this invention.

The reactor of this invention includes: vessel 1, symmetrically formed, its lower end narrowing into a point and having means 3 for controlling of a constant temperature; pipe 4 leading to the lowest part of vessel 1 for the gas supply and liquid outlet; a supply pipe 5 which extends from the upper part of vessel 1 centrally downwards to the vicinity of the center of vessel 1 for thiazolinone solution; supply pipe 6 for inert gas, conversion medium and solvent; and out-flow pipe 8 for inert gas arranged at top 7 of the cell.

Memo 3 for controlling of a constant temperature preferably consists of outer jacket 9, supply pipe 10, and outlet pipe 11 for a liquid (suitably water), which is used to keep the temperature constant. The governing of the temperature is by way of example performed by a thermostat with a circulation pump, which brings water of the desired temperature for circulation from a supply vessel through the chamber formed between jacket 9 and the outer wall of cell 1.

By means of the present invention it is possible to perform the rearrangement of the thiazolinones, formed at the automatic Edman degradation, immediately after their formation into the more stable PTH-AA derivatives. Thereby the yield of PTH-AA is increased. The sensitive thiazolinones are only to a very small extent destroyed and may in some cases be directly identified as such. The identification of PTH-argimins, PTH-histidine PTH-cystein and PTH-cysteic acid is possible in the same procedure together with the remaining PTH-AA. Hitherto these derivatives had to be separately worked and separately identified. The method is easily incorporated into the procedure of known automatic sequenators. The addition and cyclization steps in the process of such an automatic apparatus is not disturbed or delayed.

A. Feeding of the thiazolinone solution from the automatical apparatus

The chlorobutane solution of the thiazolinone (3 to 5 ml) or the column eluate from the peptide sequenator, containing the thiazolinone, respectively, is introduced through a two-way valve (not shown) into cell 1 (volume of cell 1 about 100 cm³, length 20 cm, greatest inner diameter 4.2 cm) via pipe 5, while for protection of the thiazolinone nitrogen is introduced from top through pipe 6 with the simultaneous opening of out-flow 8.

B. Drying of the Solution

Pipes 6 and 8 remain opened; also pipe 4 is opened and nitrogen is allowed to flow into the vessel from its bottom. This will prevent the solution from splashing during the evaporation process which requires about 5 to 10 minutes (temperature 55°C). Along pipe 4 there is one two-way and one three-way valve (not shown). The two-way valve is opening or closing the vessel at its bottom. The three-way valve, connected in series thereto, make possible (upon the simultaneous opening of the two-way valve) the supply of nitrogen from the bottom of the cell (supply pipe 4). If pipe 4 is closed the second pipe from this valve is opened and leads in the direction of the fraction collector (not shown).

C. Dosing of Conversion Medium 2 to 3 ml 20% aqueous trifluoro acetic acid, which contains 5 mg dithio erythrite per 100 ml, is allowed to flow into the cell (vessel) through pipe 6. The two-way valve of pipe 4 is closed, pipes 6 and 8 remain opened, stream of nitrogen is maintained. As soon as the addition is completed, pipe 4 is reopened and nitrogen flows into the cell also from bottom. After 30 to 35 minutes the cell is dry.

D. Transferring the PTH-AA into the Fraction Collector

Through pipe 6, simultaneously with the nitrogen supply, 3 ml of a mixture of 7 parts 1,2-dichloroethane and 3 parts of volume methanol are added. By means of nitrogen flow the solvent is splashed all over the surface of cell 1 in order that all of the dried substance is washed off and dissolved. Then the solution is drawn off through pipe 4 to the fraction collector by simultaneously opening of the two-way valve. Pipe 8 is then closed; however the nitrogen supply through pipe 6 is maintained. The washing and drawing off is then repeated in the same way.

E. Vacuum in Cell 1

Pipe 8 is connected to the vacuum to empty, by suction the supply pipes from the valves into cell 1. Moreover, the tightness of the valves and connections can be tested.

Cell 1 is now in order to receive the thiazolinone of the next degradation step.

We claim:

1. In a method for automatically converting a thiazolinone amino acid into a phenylthiohydantoin amino acid in the process of amino acid sequence analysis of proteins or peptides by heating said thiazolinone amino acid for a short period of time in acidic solution and transferring such solution into an organic solvent to form a solution which is appropriate for identification or further purification, the improvement that comprises introducing, with the continuous exclusion of oxygen, by the means of an inert gas flow, a solution of a thiazolinone amino acid, immediately after its formation in a solvent appropriate for said conversion, into a reaction vessel where it is evaporated to dryness at a temperature between 50° and 80°C., adding, while maintaining said temperature, an aqueous trifluoro acetic or dilute hydrochloric acid solution containing an SH-group containing substance selected from the group conssiting of dithioerythrite, β-mercaptoethanol, ethane dithiol, butane dithiol or butane thiol, in an amount which, at said temperature and flow through of said inert gas, completely evaporates within 30 to 40 minutes, dissolving the residue from the evaporation stage by spraying over it a mixture of 6 to 8 parts of volume of 1,2-dichloroethane and 4 to 2 parts of volume of methanol, and removing the resultant solution from said reaction vessel.

2. Method according to claim 1 wherein nitrogen is used as said inert gas.

3. Method according to claim 2 wherein dithioerythrite is used as said SH-group containing substance.

4. Method according to claim 2 wherein an aqueous solution containing 20 percent of trifluoro acetic acid and 10 to 150 mg/1 of dithioerythrite is used.

5. Method according to claim 2 wherein 1N hydrochloric acid containing 10 to 150 mg/l of dithioerythrite is used.

6. Method according to claim 2 wherein a drying temperature of 53° to 57°C. is used.

7. Method according to claim 1 wherein said inert gas is nitrogen, helium or argon.

* * * * *